(12) United States Patent
More et al.

(10) Patent No.: US 11,428,386 B2
(45) Date of Patent: Aug. 30, 2022

(54) ROTATABLE FORM SHADOW CASTING DEVICE

(71) Applicants: Michael More, Stevens Point, WI (US); John Knechtel, Iola, WI (US)

(72) Inventors: Michael More, Stevens Point, WI (US); John Knechtel, Iola, WI (US)

( * ) Notice: Subject to any disclaimer, the term of this patent is extended or adjusted under 35 U.S.C. 154(b) by 75 days.

(21) Appl. No.: 17/091,806

(22) Filed: Nov. 6, 2020

(65) Prior Publication Data
US 2021/0140609 A1    May 13, 2021

Related U.S. Application Data

(60) Provisional application No. 62/932,384, filed on Nov. 7, 2019.

(51) Int. Cl.
| | | |
|---|---|---|
| *F21V 33/00* | (2006.01) | |
| *F21V 14/08* | (2006.01) | |
| *A61M 21/00* | (2006.01) | |
| *A61M 21/02* | (2006.01) | |
| *F21S 10/00* | (2006.01) | |
| *F21W 121/00* | (2006.01) | |

(52) U.S. Cl.
CPC ............ *F21V 14/08* (2013.01); *A61M 21/02* (2013.01); *A61M 2021/0044* (2013.01); *F21S 10/00* (2013.01); *F21V 33/0056* (2013.01); *F21W 2121/00* (2013.01); *Y10S 362/806* (2013.01)

(58) Field of Classification Search
CPC .......... F21V 14/08; F21V 1/10; F21V 17/002; F21V 33/0056; F21S 10/00; F21S 10/007; F21S 9/00; Y10S 362/802; F21W 2121/00; A61M 21/02; A61M 2021/0044
See application file for complete search history.

(56) References Cited

U.S. PATENT DOCUMENTS

| | | | |
|---|---|---|---|
| 5,517,264 | A | 5/1996 | Sutton |
| 7,438,446 | B1 | 10/2008 | McCann |
| 7,473,002 | B1 | 1/2009 | Chen |
| 8,317,359 | B2 | 11/2012 | Harbers et al. |
| 9,068,726 | B2* | 6/2015 | Zhang .................... F21S 10/00 |
| 9,395,061 | B2 | 7/2016 | Yang |
| 9,551,472 | B2* | 1/2017 | Ding .................... F21S 10/007 |
| 9,664,373 | B2* | 5/2017 | Zhang .................... F21V 14/06 |
| 9,857,061 | B1 | 1/2018 | Deng |
| 2013/0308315 | A1* | 11/2013 | Capitani ............. F21V 33/0056 362/253 |
| 2018/0310743 | A1* | 11/2018 | Abukar ............... F21V 33/0056 |

* cited by examiner

*Primary Examiner* — Y M. Quach Lee
(74) *Attorney, Agent, or Firm* — Brandon Carlin (57) ABSTRACT

A light emitting device with a rotating form thereon, said device having a motor and a power source contained within a generally durable housing having a lens and an elongated spire extending outside of the durable housing and through an opening contained within the lens, said elongated spire additionally having a decorative rotatable form positioned on a distal end of the elongated spire, and at least one light source directing emitted light at the rotatable form, such that crisp hard shadows are produced on outlying surfaces. A power source is provided, connected to a motor and processor so as to move or rotate the spire and thus the form, causing the lights to cast moving decorative shadows on an exterior surface.

20 Claims, 8 Drawing Sheets

ROTATABLE FORM SHADOW CASTING DEVICE

CROSS REFERENCE TO RELATED APPLICATION

This application claims the benefit of U.S. Provisional Application 62/932,384, filed Nov. 7, 2019.

FIELD

The present disclosure is directed to the field of generalized illumination devices, and more particularly to a new and useful device for creating casting shadows which are illuminated on a flat surface.

BACKGROUND

Many persons struggle with their ability to fall asleep. Numerous issues can cause a person to be able to finally get to sleep, and one of the most prevalent issues is racing thoughts. When a person is thinking too much or focusing mentally on a number of different issues, their capability to rest is severely degraded.

Babies make up one group of persons that struggle with racing thoughts. It is thought that babies are so mentally stimulated by many different things that they sometimes cannot get to sleep quickly, to the detriment of their parents. Most parents prefer their child to be on a sleep schedule so that the parents themselves may get rest at night. However, when a baby is intrigued by something they see, they may also desire their parents to be near such that the baby wishes for the parent to share in the experience. This can lead to crying spells and refusal to be laid down to rest in a crib.

Further, a small child or infant may be afraid of the dark, and not being able to see anything frightens them such that the affected child cries until their parent can come back and comfort them. To help combat this fear, a night light may be used so that the child can have the ability to look around. Unfortunately, the capability of sight then may cause the child to be fascinated or curious about something they can see, and the issues of racing thoughts as described above can manifest.

A baby mobile, or crib mobile, is a method to provide entertainment and visual stimulation for a child. These mobiles are typically rotational devices that a child can look at. However, over time a child may bore of the repetitive nature of the mobile, and the aforementioned night light is a requirement so that a child can see the mobile itself should the room be darkened.

What is needed, therefore, is a device which can properly illuminate an area in a room to prevent nighttime fears, while also employed visually stimulating imaging to avoid racing thoughts.

BRIEF SUMMARY

The present disclosure is directed to an illumination device that has a rotatable form or projection form, with lighting projected thereon, in order to project said lighting at various adjustable angles creating high-contrast shadows. The device contains an upwards facing generally centrally located shaft, otherwise known as an obelisk or an elongated spire, which can simultaneously receive and hold a rotating form such that the light emitted thereon projects high-contrast layers of lighting and shadows onto a surface.

The rotatable form shadow casting device is comprised of a generally durable material, such as plastic, metal, a metal alloy, or any other generally rigid material which is preferably resistant to general wear and tear. The durability provided by the material also allows for sustainability, and the ability to withstand typical blunt force associated with accidental dropping from a vertical height.

The present disclosure is directed to a rotatable form shadow casting device that has a lower housing unit which in one embodiment comprises support legs, or it may be mounted to a surface such as a wall by way of a bracket. However, the lower housing unit may additionally contact with a resting surface. In such a fashion, the upper housing unit provides general rotational adjustment and repositioning in multiple horizontal axes, in a general mortar and pestle rotation.

The lower housing unit removably receives an upper housing unit, and when the two housing units are mated together, also known as removably coupled, it is known herein as a housing unit. In some embodiments, there is only a housing unit. This is one piece of material that is formed, created, or shaped. A housing cavity exists therein and to access the components the lens must be removed. Both the lower and the upper housing units are generally hollow, similar to a toy Easter egg, a housing cavity is formed between the two housing units when mated together. This housing cavity is thus where the internal components of the device are placed, to be protected against outside elements The upper housing unit has an open top end. This open top end is substantially covered by a lens, or a protective film, cover, or material that it is generally transparent or translucent. The lens is preferably water-resistant and has a hole or an opening in the approximate center thereof.

The previously mentioned elongated spire is positioned in the housing cavity at one end and extends through the opening of the lens and outside of the housing cavity at the spire opposing end, as depicted later in the drawings. The elongated spire additionally has a form on the end thereof. It is contemplated that the spire may have a ball bearing at the distal end outside of the housing cavity, whereupon a removable and interchangeable rotatable form is generally connected or rested upon.

An alternative embodiment specifically contemplated herein has the form attached or formed on said spire distal end, creating a shape similar to a T, otherwise known as a tau-shape. In this alternative embodiment, the spire itself is interchangeable and removable, to allow for multiple variants of form design. This will provide for different designs, shapes, patterns, and contrasts being projected on the surface. Thus, the rotating form allows for a decorative shadow or decorative light as the case may be, to be projected. The rotating form may be interchangeable with other designs of the form itself, such that there are numerous options of decorative shadows to prevent repetition. Thus, the shape of the form itself is directly correlated to the shape of the decorative shadows, and the rotational speed and the speed of the revolution of the decorative form allows for multiple varieties of imaging to be projected. An intent is to cast a shadow with a high degree of contrast, complete with a fluid movement thereof directly related to the rotation or movement of the spire and thus the form thereon. Additionally, creating layers of projected shapes and allowing for the changing of the amount of contrast is presently thought to have the most effective display of shadows.

Positioned within the housing cavity, and thus protected from outside forces, are the components of the rotatable form shadow casting device. A motor is provided within the housing cavity. The motor may be any type of motor to stay within the spirit of the disclosure, such as a stepper motor, a servo motor, a printed circuit board motor, or a dc brushless to name a few of the satisfactory options. The motor is coupled to the spire, which will allow for rotation of the spire, and thus the form thereon.

The motor may be attached or otherwise coupled or connected to a housing plate for stability. The housing plate may have bushings or bearings, such as a bearing plate. The plate will provide stability to the motor and the first end of the spire.

A plurality of light sources are provided within the housing cavity. The light sources may be a variety of different types and be within the spirit of this disclosure, such as a light-emitting diode, plasma, laser, incandescent, or halogen, to name a few. An emerging light technology such as micro LEDs would function as required within this disclosure. One with skill in the art would know that a variety of other light sources would also work to obtain the same effect as intended herein.

The plurality of light sources may be arranged in any desired pattern within the housing cavity. One option would be to have a radial pattern as from the elongated spire, but other options such as an imbalanced pattern, a linear arrangement, or other design could work to achieve the high-contrast shadows as desired. In so doing, one reason for doing would be to create an asymmetrical view or design which still creates high contrast and designed shadow imaging, as is an objective of the present disclosure.

An audio driver may be provided which allows for sound to be emitted if so desired. This audio driver can play a variety of different music and may further encompass a microphone to detect noises emitted. Additionally, with a speaker and a microphone, it is contemplated that what is known as a baby monitor may be thus installed within the housing cavity to allow users to communicate through radio frequencies, power line, transmitting line, or other technologies. In a similar sense, it is contemplated that the baby monitor function can be further enhanced with the printed circuit board such that if a certain frequency volume or pitch is detected, such as that of a crying infant, the device can automatically turn on for a set period of time.

It is presently thought that a housing plate may be utilized in some embodiments, along with a corresponding heat sink, or plurality thereof to absorb heat, should the device require it, to keep components cooler inside the housing cavity.

In such a matter, the device of the present disclosure allows for a decorative shadow created on the projected horizontal or vertical surface which enables visual stimulation, and the surrounding illumination thereof eliminates the need for an additional night light. The resulting decorative illumination establishes a relaxing image that facilitates calmness and associated relaxation therefore.

These and various other features, advantages, modes, and objects of the present invention will be made apparent from the following detailed description and any appended drawings.

BRIEF DESCRIPTION OF THE DRAWINGS

One or more preferred exemplary embodiments of the present disclosure are illustrated in the accompanying drawings in which like reference numerals represent like parts throughout and in which.

Before explaining one or more embodiments of the disclosed invention in detail, it is to be understood that this invention is not limited in its application to the details or modes of construction and the arrangement of the components set forth in the following description or previously disclosed illustrations. This invention is capable of multiple embodiments and modes, which can be practiced or carried out in many various ways. Also, it is to be understood that the phraseology and terminology employed herein is for the purpose of description, and should not be regarded as limiting, or used as an absolute.

DETAILED DESCRIPTION

Figure 1:
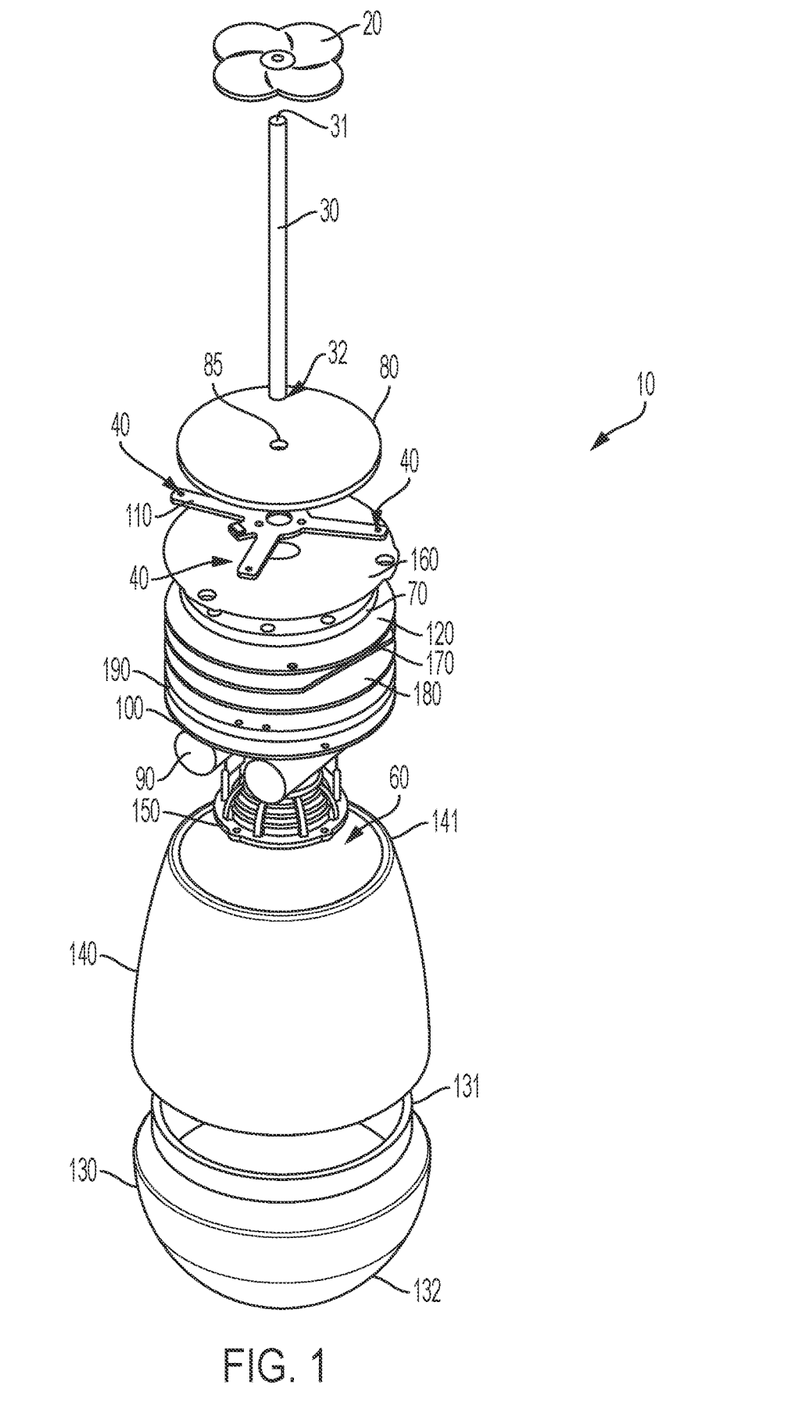
FIG. 1 is an exploded view of an embodiment of the Rotatable Form Shadow Casting Device.

Referring now to the drawings in detail, FIG. 1 illustrates a preferred embodiment of a rotatable form shadow casting device 10 constructed in accordance with the present invention. This embodiment is an exploded view and is shown with a lower housing unit 130 having a bottom end 132 and a top end 131. The upper housing unit 140 couples to the lower housing unit 130. The components that are contained within the housing cavity 60 are displayed outside and above the upper housing unit top end 141 and said housing cavity 60, though when assembled they reside therein.

Figure 4:
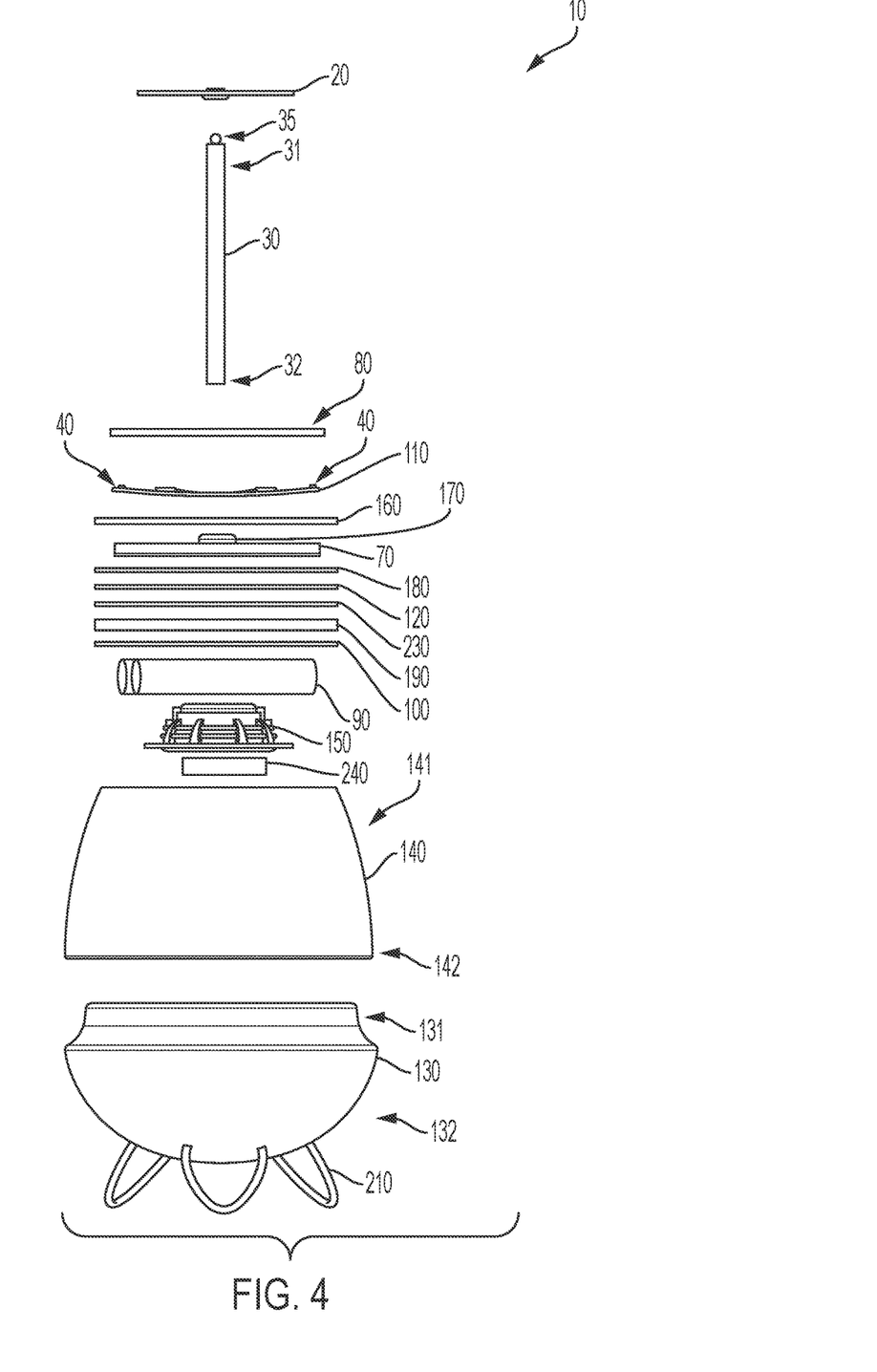
FIG. 4 is a side exploded view of an embodiment of the Rotatable Form Shadow Casting Device.

A speaker 150 is depicted, which may transmit audio signals. Contained within or near the speaker 150 may be an audio driver or said audio driver may be on the processor 130, as depicted in FIG. 4. The speaker 150 may additionally be a two-way speaker containing a microphone therein, or the microphone may be a separate component in another location within the housing cavity 60. As earlier-discussed, the processor 230, as shown in FIG. 4, may convert saved and stored audio files into audio signals that can be played as songs or tunes by the speaker 150 which may be relaxing or calming to a human user. Should the use be as a two-way speaker or baby monitor, the speaker may be utilized to transmit human voice or other external sounds.

Figure 8:
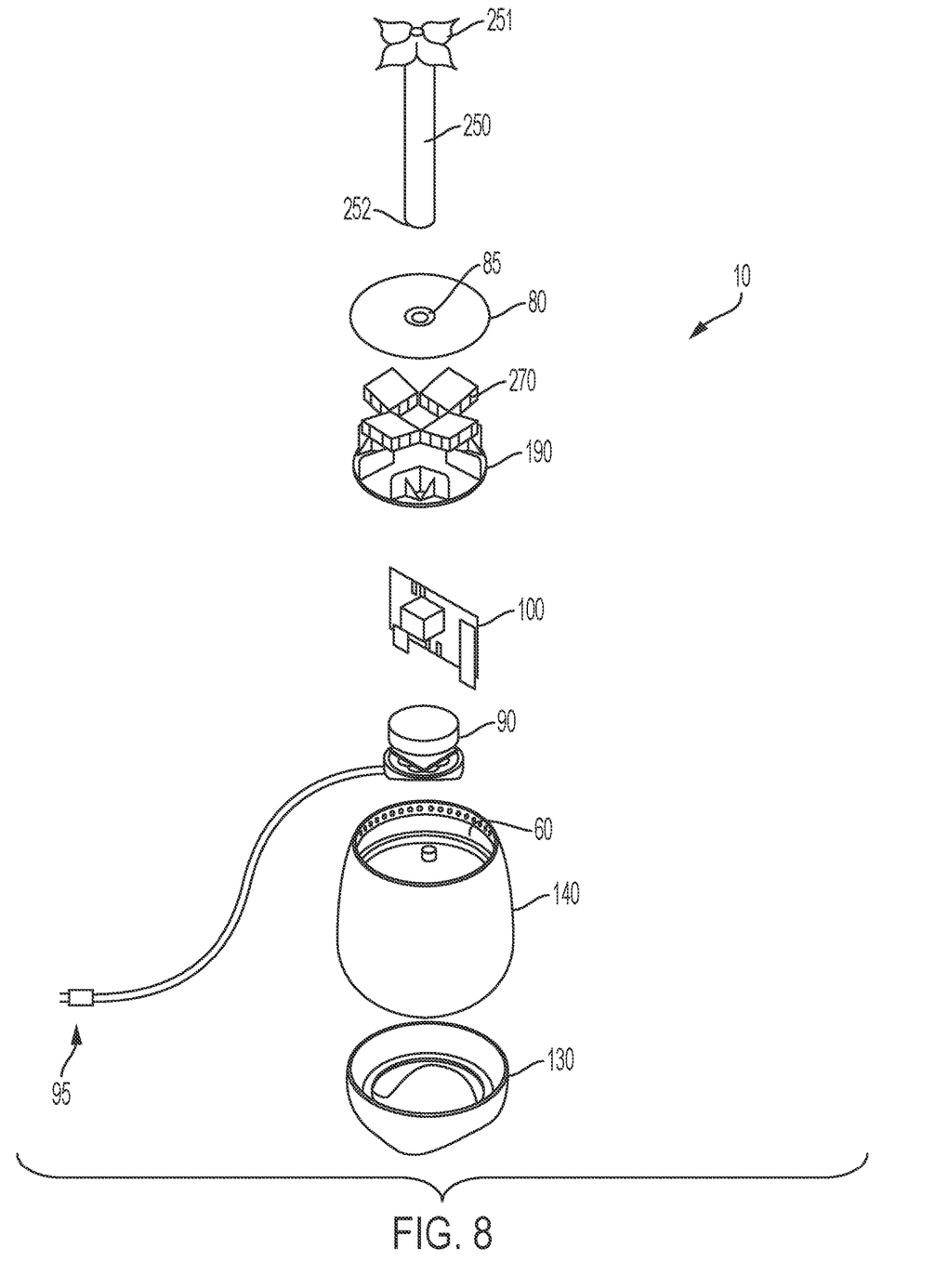
FIG. 8 is an exploded view of an embodiment of the Rotatable Form Shadow Casting Device, where a tau-shaped elongated spire is utilized.

Also shown here in FIG. 1 is a power source 90, which may be various types of batteries such as electric, alkaline, lithium, nickel cadmium, or may consist of a capacitor, and there may also be a power source cord 95, as shown in FIG. 8. The power source here in FIG. 1 has a printed circuit board 100, which may additionally contain a charging circuit so as to charge a battery when not at full power, as well as fuses and/or temperature sensing devices. The power source 90 may be coupled to the motor 70 to provide power thereto and is contained or positioned within the housing cavity 60.

A motor 70 is depicted, which is coupled to an elongated spire 30 at the elongated spire second end 32, also known as the bottom end of the elongated spire 30, or the end which couples with the motor 70. The elongated spire 30 may be rotated using different methods in order to achieve the desired effect of cast shadows. The elongated spire is preferably made from a durable material.

The motor 70, as described above, could be a variety of different types, such as the ones listed above, or a general electric motor or a DC motor. The motor 70 may, particularly if it is an electric motor, contain a rotor 170 and a stator 180. It is presently contemplated that should the motor 70 utilize a rotor 170, permanent magnets will be utilized as the moving component of the motor 70, and be coupled or otherwise mechanically connected to the elongated spire second end 32, to allow movement or rotation thereto. Further, additional magnetic material may be added to the rotor 170 or the stator 180, so as to improve efficiency of the motor 70.

The motor 70 in this embodiment is connected to an additional printed circuit board 120 which provides drive signals to the motor 70. In this embodiment, the motor 70 is mounted or attached to a housing plate 190. As specified above, the housing plate 190 may have bushings or be a bearing plate. The housing plate 190 works to stabilize the motor 70 and the elongated spire 30 which is coupled thereto.

Figure 7:
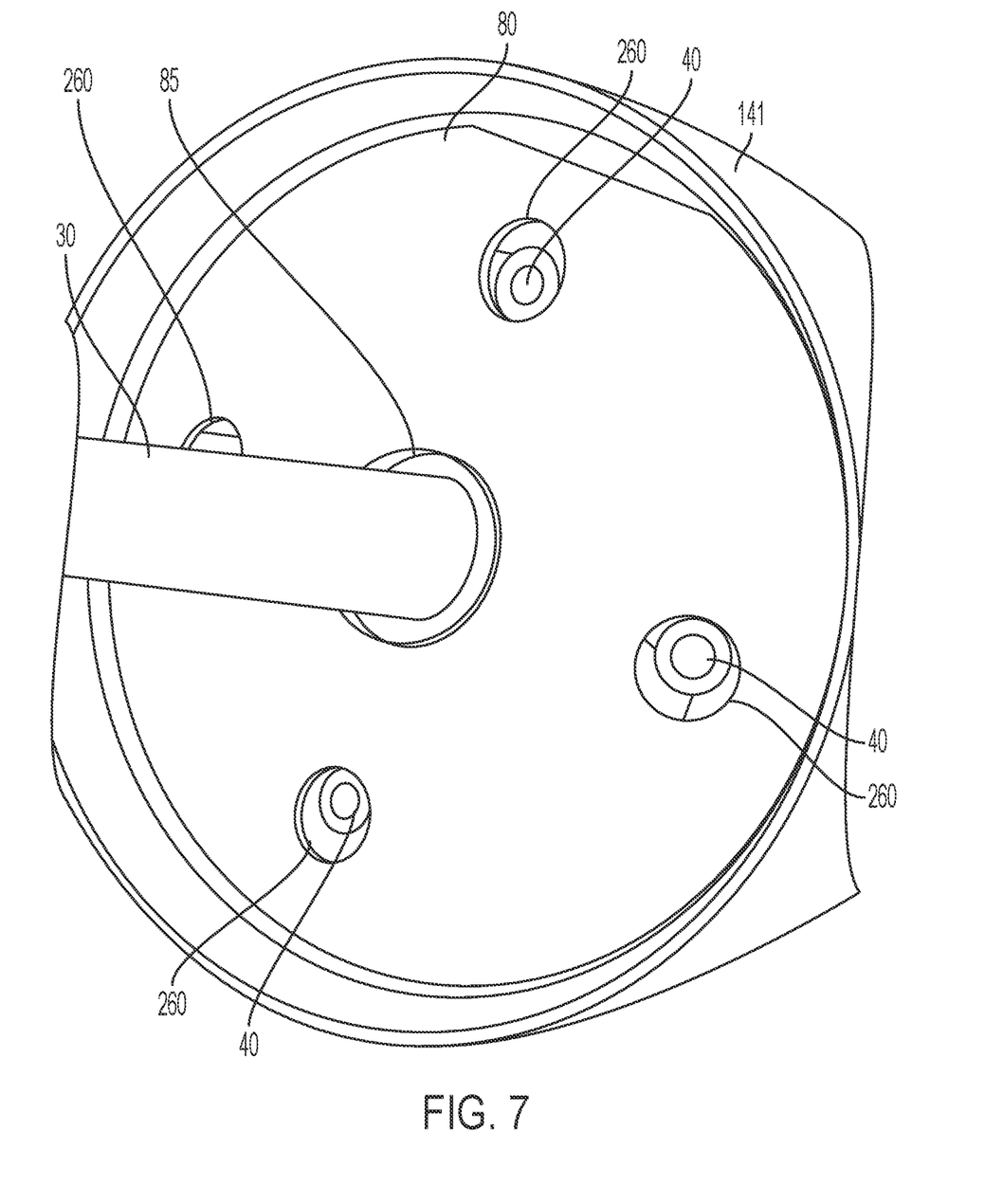
FIG. 7 is a perspective view of an embodiment of a lens, highlighting outport port openings, and light sources.

A support plate 160 is shown in this drawing, with a flexible printed circuit board 110 thereon. While this particular circuit board 110 is flexible, this is not a requirement. A plurality of light sources 40 are attached or affixed to the flexible printed circuit board 110, and are directed generally towards a rotatable form 20 which is on the distal first end of the elongated spire 31, outside the housing cavity 60, as will be explained in more detail below. The direction of the light sources 40 may be directly related to output port openings 260, as shown in FIG. 7. Additionally, the positioning of the light sources 40 should be such that the light is projected or emitted generally at the rotatable form 20. When the light sources 40 are affixed, mounted, or attached to the flexible printed circuit board 110, as here, the flexible printed circuit board 110 is strategically maneuvered in such a way so as to accomplish the previously-mentioned purpose of emitting light at or generally near the rotatable form 20.

The support plate 160 may be used to secure the electronics assembly within the housing cavity 60, and may additionally contain a bearing holder so as to stabilize the elongated spire 30.

A lens 80 is shown in this exploded view, having an opening 85 in a generally central location thereon. This opening 85 allows the elongated spire 30 to pass through into the housing cavity 60 on the spire second end 32, and project away from said cavity 60 on the other first end 31. It is on the first end 31, that the rotatable form 20 is attached, affixed, formed, or placed. Additionally, the lens 80 may have a decorative design thereon so as to create a background display of light on the exterior surface upon which the shadows are cast. The lens 80 is generally transparent or translucent such that light may pass therethrough. Further, the lens 80 should substantially cover the light sources 40, so as to minimize direct line-of-sight of a human user thereto, as well as to prevent exterior contaminants from contacting or entering thereon.

When the motor 70 is activated, the spire 30 is rotated or moved, which due to the direct relationship between the spire 30 and the rotatable form 20, causes the form 20 to move or rotate as well. The form 20 is interchangeable and may be connected to the elongated spire first end 31 by way of magnets, or rest on a ball bearing, use of gravity, or any other removable connected method, to stay within the spirit of the invention. The design of each form 20 is directly related to the type and design of a cast shadow on an exterior surface, so interchangeability of different designs of forms 20 thus allows for interchangeability of design of shadows cast.

The light sources 40 are generally directed at the form 20, such that light emitted from the light sources 40 strike the form 20. The light waves which do not strike the form 20, continue to pass onto a surface, such as a wall or ceiling for example, creating a shadow on said surface. As the spire 30 and thus the form 20 moves or rotates, the shadow itself transmutes or evolves or changes its abstract shapes.

Figure 2:
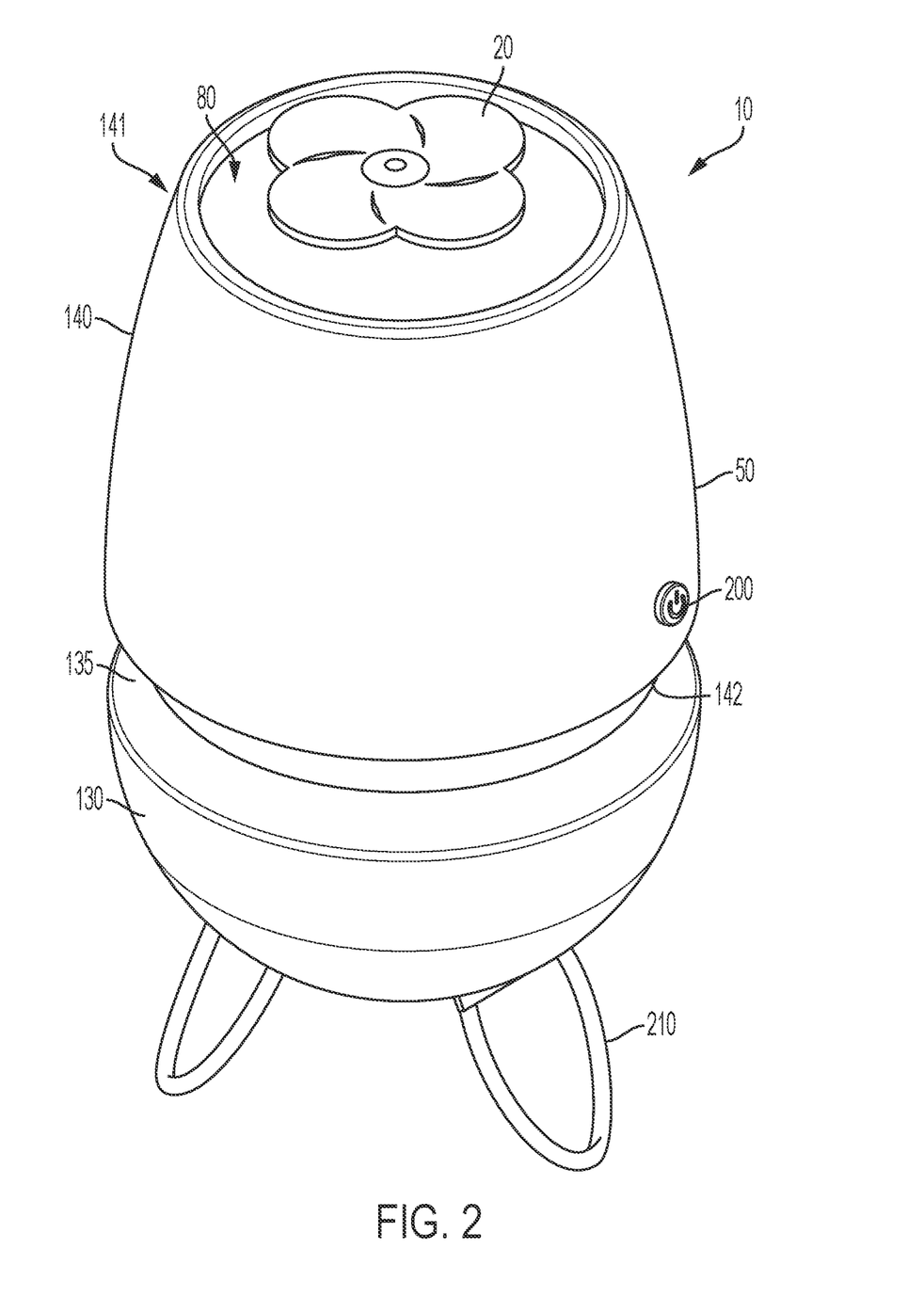
FIG. 2 is a perspective side view of an embodiment of the Rotatable Form Shadow Casting Device.

Turning now to FIG. 2, the rotatable form shadow casting device 10 is shown in a perspective view wherein the lower housing unit 130 and the upper housing unit 140 are coupled together, create a closed shell known as the housing unit 50. A user interface button 200 is shown here on the exterior of the housing unit 50, which may consist of a power button, or a plurality of buttons such as a volume button, light intensity button, skip track, or any other type of interface that would be preferable. The user interface button 200 may also be a dial, dimmer switch, or touch display.

In this particular embodiment, a housing unit cord wrap area 135 is also depicted, in a place between the upper housing unit bottom end 142 and the lower housing unit top end 131. Should an embodiment utilize a power source cord 95, such as shown in FIG. 8, said power source cord 95 may be wrapped in the hosing unit cord wrap area 135 for ease of portability or to reduce space in packaging. On the exterior of the housing unit 50 support legs 210 are provided in this embodiment, which may be adjustable or tiltable. It is contemplated that to achieve an adjustment, or a tilt, the support legs 210 may be articulating such that they are capable of folding inward towards the rotatable form shadow casting device 10 in a form of adduction. As used herein, the terms adjustable and tiltable mean that the support legs 210 may adjust their vertical or horizontal position, which directly correlates to the positioning of the lower housing unit bottom end 132 in a y-axis or x-axis as view in a tri-dimensional space. By way of example, the tilting or adjusting of said support legs 210 are illustrated in FIG. 3.

Figure 3:
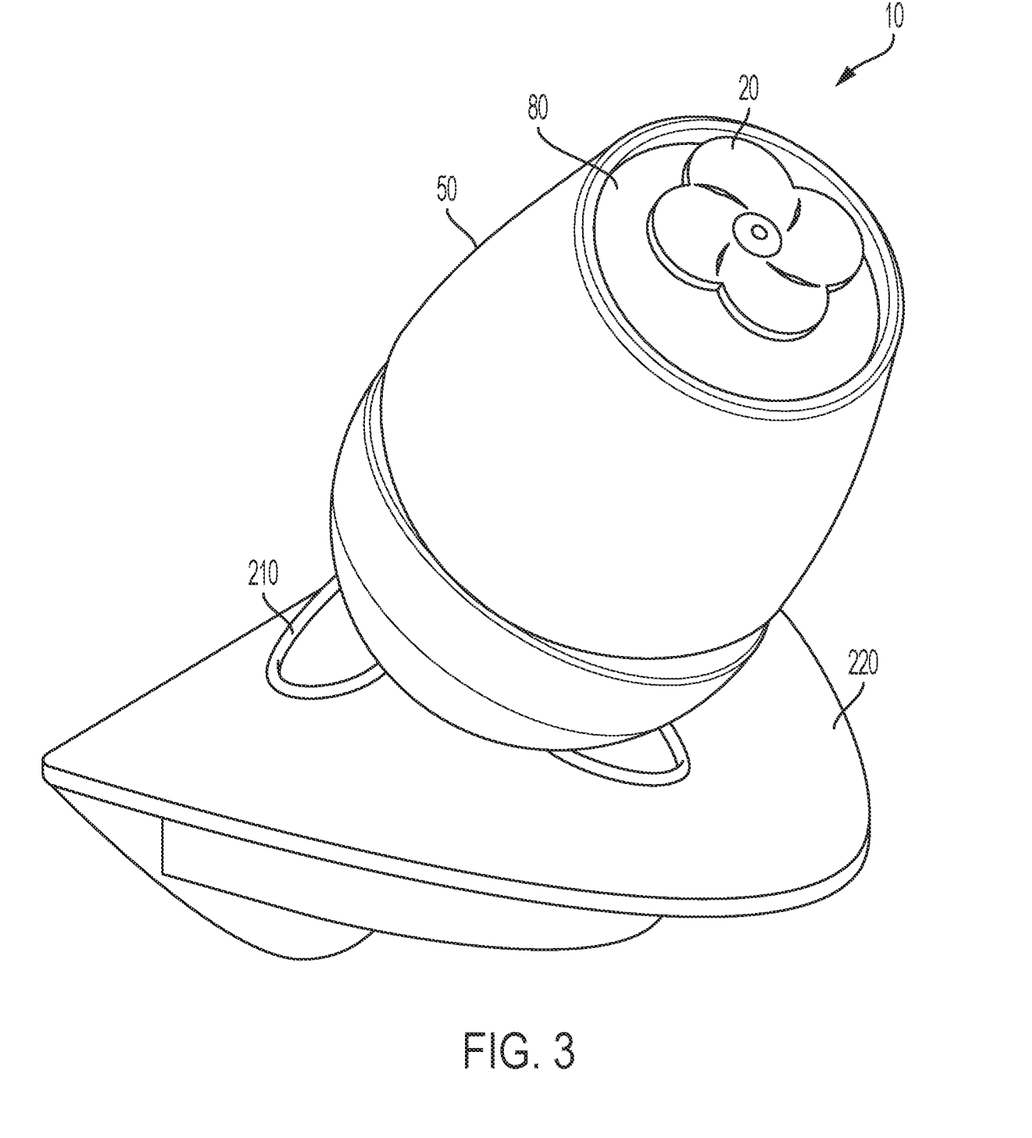
FIG. 3 is a perspective side view of an embodiment of the Rotatable Form Shadow Casting Device showing an example of a wall bracket unit, and additionally highlighting tiltable support legs.

Staying on FIG. 3, an embodiment of the rotatable form shadow casting device 10 is shown utilizing not only the tilting or adjusting of the support legs 210 as just described, but also shows one form of a wall bracket 220. This particular figure illustrates the housing unit 50 of the rotatable form shadow casting device 10 at an angle due to the adjustment of the support legs 210, to strategically place the to-be emitted shadow on a determined location of a surface beyond. The wall bracket 220 moves the placement of the rotatable form shadow casting device 10 to a vertical position, preventing unintentional contact, allowing for use when an appropriate horizontal support is not readily available, as well as from other objects intersecting the points of the form and from the projected surface, which would cause accidental additional shadows to be projected.

Look now to FIG. 4. This is a side exploded view of an embodiment of the rotatable form shadow casting device 10 whereupon support legs 210 are placed near the lower housing unit bottom end 132. The rotational form 20 is positioned above the elongated spire 30, whereupon a ball bearing 35 is placed upon or within the elongated spire first end 31.

Within the exploded view herein is a processor 230. A processor 230 may be used to provide signals to the motor 70, allowing for varying drive signals. In such a fashion, content file information in the processor 230 may additionally control other components herein, such as the light sources 40, a speaker 150, a microphone, a Bluetooth device, or a remote-control interface 240. In a similar fashion, the processor 230 may contain a storage medium so as to hold information such as flash memory, with appropriate RAM. This allows the rotatable form shadow casting device 10 to have multiple songs for the speaker 150 to play, varying rotational rhythms for the motor 70 to rotate the elongated spire 30, and even different pulsing of the light sources 40, wherein some of the plurality of light sources 40 turn off and alternatively turn on, ramping, or fading at predetermined time sequences. Should the desired effect be to alternatively activate or deactivate some or all of the plurality of light sources 40, the processor 230 may provide signals so as to accomplish this desired effect, or it may be provided by the microphone should a user desire.

Software is utilized by the processor 230 to handle loading of content files, and allow for the setting, updating, and use of various parameters such as feedback loops, scheduled power on or scheduled power off, or other user-controlled or scheduled parameters. The software will manage and control the power input, charging, and battery operation as well as to monitor and select the appropriate mode of operation and configuring of any power supply hardware, if applicable.

A remote control interface 240 may be provided as shown here, which will allow a human user to control various aspects of the rotatable form shadow casting device 10, by way of example some aspects which may be controlled are the power to the device 10 itself, the motor 70 rotational speed, the motor 70 rotational rhythm, the speaker 150 volume, or the audio driver songs. It is specifically contemplated herein that the remote-control interface 240 is a Bluetooth adaptable device, such that the rotatable form shadow casting device 10 is able to be controlled via a Bluetooth device such as a smartphone application. Additionally, it is presently contemplated that the remote-control interface 240 has Wi-Fi capability, so as to be controllable in such a fashion. In another alternative embodiment, the remote-control interface 240 is on one, or one of the printed circuit board(s).

Figure 5:
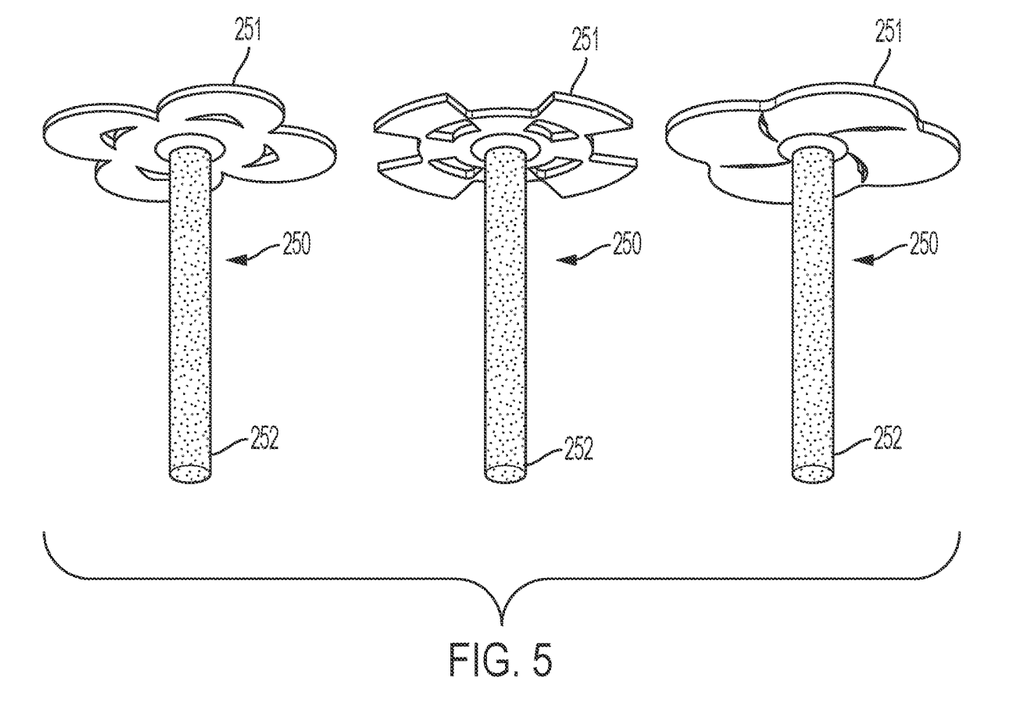
FIG. 5 is a perspective view of embodiments of interchangeable tau-shaped elongated spires.

Now turning to FIG. 5, variations of tau-Shaped Elongated Spires 250 are depicted. As discussed earlier, the tau-shaped Elongated Spires 250 are constructed of generally solid material and have a second end 252 and a first end 251, upon which a form is attached, mounted, or formed. In this particular embodiment, as can be appreciated in FIG. 8, the tau-shaped elongated spire 250 itself is interchangeable, removably coupled to the motor so as to allow for different variations and thus different shadow effects being displayed on the surface.

Figure 6:
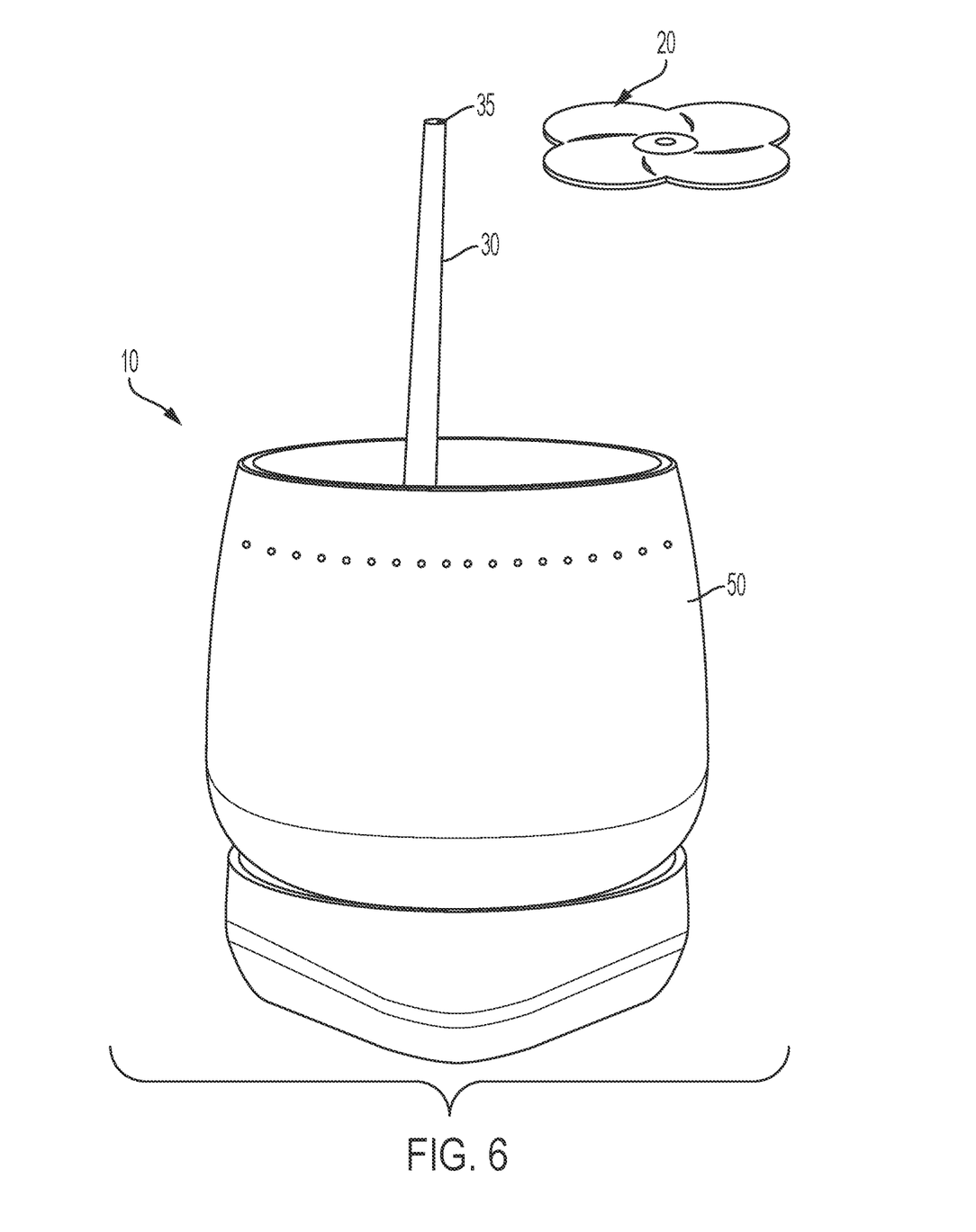
FIG. 6 is a perspective view of an embodiment of the Rotatable Form Shadow Casting Device wherein the rotatable form has been removed during the process of interchanging.

FIG. 6 shows a variation of the rotatable form shadow casting device 10 in which the housing unit 50 is displayed as a singly formed piece of material, as described in detail above. with the ball bearing 35 on the elongated spire 30 exposed, as it is in the middle of the process of interchanging forms.

Moving to FIG. 7, a closeup view of the lens 80, is shown, wherein the elongated spire 30 is also depicted emerging and extending beyond the lens opening 85. This figure shows multiple output port openings 260, which are known and defined herein as additional openings within the lens 80, such that the light sources 40 contained within the housing cavity 60, as shown in FIG. 1 and FIG. 8, are able to transmit and emit light therethrough. The output port openings 260 may be machined, formed, or not printed/obstructed such that light may easily pass therethrough. It is contemplated that the lens 80 may be removable or replaceable such that different ornamental designs may be placed thereon, or alternatively, the lens 80 may be of various colors, such that the light emitted from the plurality of light sources 40 changes color, hue, or visual appearance. The plurality of light sources 40 may additionally comprise alternative color schemes such as different colored light sources to affect color, hue, or visual appearance.

Lastly, we look to FIG. 8. On this image, an exploded view of an embodiment of the rotatable form shadow casting device 10 is illustrated, wherein the lower housing unit 130 at the bottom of the image has a generally open lower housing unit bottom end 132, and an open top end 131, so as to receive and couple with the upper housing unit 140. Within the housing cavity 60 are the inner components of the rotatable form shadow casting device 10, however said components are displayed above in this exploded view. The power source 90 here additionally comprises a power source cord 95, as was referred to earlier. The power source cord may be a utility power, or a 110V plug, or a USB connection, or any other type of adaptable power supply cord. A printed circuit board 100 is shown with other processor 230 components thereon. A housing plate 190 is also depicted, in this embodiment with exterior heat sinks 270 located near the not-visible plurality of light sources 40 that help to keep the components cool. Located above this is the lens 80 with lens opening 85, such that the tau-shaped elongated spire 250 may be received. In this particular embodiment, the housing unit 50 is adjustable similar to a mortar and pestle, wherein the upper housing unit 140 rotates within the lower housing unit 130, on multiple axis therein.

Understandably, the present invention has been described above in terms of one or more preferred embodiments and methods. It is recognized that various alternatives and modifications may be made to these embodiments and methods that are within the scope of the present invention. Various alternatives are contemplated as being within the scope of the present invention. It is also to be understood and appreciated that, although the foregoing description and drawings describe and illustrate in detail one or more preferred embodiments of the present invention, to those with skill in the art to which the present invention relates, the present disclosure will suggest many modifications and constructions, as well as widely differing embodiments and applications without thereby departing from the spirit and scope of the invention and method disclosed thereof.

What is claimed is:

1. A light emitting device, comprising:
   a lower housing unit with a bottom end and an open top end;
   an upper housing unit having an open bottom end and an open top end, wherein the upper housing unit is removably coupled at the open bottom end to the open top end of the lower housing unit, defining a cavity therein;
   a housing plate positioned within said housing cavity;
   a first circuit board attached to said housing plate;
   a motor attached to the housing plate;
   a power source coupled to the motor and contained within said housing cavity;
   a second circuit board attached to said motor;
   a plurality of light sources positioned on said second circuit board;

a lens attached near the upper housing unit top end, wherein said lens additionally comprises a centrally located opening; and a generally tau-shaped elongated spire having a first end and a second end, wherein said elongated spire second end is coupled to said motor and said elongated spire first end comprises a form at a distal end and further projects through and outside the entirety of the lens opening.

2. The light emitting device of claim 1, wherein said rotatable form rotates around an axis created by the elongated spire when the motor is actuated.

3. The light emitting device of claim 2, wherein said plurality of light sources are positioned such that light emitted therefrom is generally projected at the rotatable form.

4. The light emitting device of claim 3, wherein said light sources are one of:
light-emitting diode, plasma, laser, incandescent, and halogen.

5. The light emitting device of claim 4, additionally comprising a speaker within the housing unit cavity.

6. The light emitting device of claim 5, wherein said housing unit additionally comprises a microphone.

7. The light emitting device of claim 6, wherein said lens additionally comprises a plurality of output port openings.

8. The light emitting device of claim 7, additionally comprising a remote-control interface.

9. A rotatable form light projecting device, comprising:
a lower housing unit having a bottom end and an open top end;
an upper housing unit having an open bottom end and an open top end, wherein the upper housing unit is removably coupled to the open top end of the lower housing unit at the upper housing unit open bottom end, defining a cavity therein;
a bearing holder within said housing unit cavity;
a first printed circuit board attached to said bearing holder;
a motor electronically connected to said first printed circuit board;
a power source coupled to the motor and contained within said housing cavity;
a flexible printed circuit board attached to said motor;
a plurality of light sources positioned on the flexible printed circuit board;
a lens attached near the upper housing unit open top end, wherein said lens additionally comprises an opening therein; and
a generally tau-shaped elongated spire having a first end and a second end, wherein said elongated spire second end is coupled to said motor and said elongated spire first end comprises a form at a distal end and further projects through and outside the entirety of the lens opening.

10. The rotatable form light projecting device of claim 9, wherein said plurality of light sources are positioned such that all light sources emit light generally at the first end of the tau-shaped elongated spire.

11. The rotatable form light projecting device of claim 10, wherein said tau-shaped elongated spire rotates around an axis created by said elongated spire.

12. The rotatable form light projecting device of claim 11 further comprising a second printed circuit board positioned within said housing cavity and wherein said second printed circuit board is electronically connected to the power source.

13. The rotatable form light projecting device of claim 12, further comprising a processor positioned within said housing cavity.

14. The rotatable form light projecting device of claim 13, wherein said tau-shaped elongated spire is removable.

15. A rotational form light projector, comprising:
a housing unit having a bottom end and an open top end, said housing unit defining a cavity therein;
a power source positioned within said housing unit cavity;
a first printed circuit board electronically connected to said power source;
a bearing holder positioned within said housing unit cavity;
a processor attached to the bearing holder;
a second printed circuit board positioned within said housing unit cavity;
a motor having a stator and a rotor, said motor electronically connected to said second printed circuit board;
a support plate positioned betwixt said stator and said housing unit open top end;
a printed circuit board positioned on the support plate;
a plurality of light sources positioned on said flexible printed circuit board;
an elongated spire having a first end and a second end, wherein said second end is coupled to the motor;
a rotatable form removably connected to the first end of the elongated spire;
a lens surrounding the elongated spire betwixt the elongated spire first end and the elongated spire second end, and further comprising a plurality of output port openings directly proportional to each of the plurality of light sources; and
wherein each of said light sources is positioned such that light emitted therefrom is generally directed towards the rotatable form.

16. The rotational form light projector of claim 15, additionally comprising a speaker located within the housing unit cavity.

17. The rotational form light projector of claim 16, wherein said housing unit additionally comprises a microphone.

18. The rotational form light projector of claim 17, additionally comprising a user interface button located on the housing unit.

19. The rotational form light projector of claim 18, comprising a plurality of support legs located on the housing unit.

20. The rotational form light projector of claim 19, additionally comprising a wall bracket located on one of the housing unit and the support legs.

* * * * *